United States Patent [19]

Humphreys et al.

[11] Patent Number: 5,358,656
[45] Date of Patent: Oct. 25, 1994

[54] COMPOSITIONS COMPRISING GLYCEROGLYCOLIPIDS HAVING AN AMINE LINKAGE AS A SURFACTANT OR COSURFACTANT

[75] Inventors: Robert W. Humphreys, Oradell, N.J.; Anthony Hung, New City, N.Y.; Shang-Ren Wu, Mahwah, N.J.; Abid N. Khan-Lodhi, Hoole Chester, England

[73] Assignee: Lever Brothers Company, Division of Conopco, Inc., New York, N.Y.

[21] Appl. No.: 982,199

[22] Filed: Nov. 25, 1992

Related U.S. Application Data

[63] Continuation-in-part of Ser. No. 816,423, Dec. 31, 1991.

[51] Int. Cl.$^5$ ............................................. C11D 3/22
[52] U.S. Cl. ........................ 252/174.12; 252/174.17; 252/DIG. 12; 252/108; 536/4.1; 536/17.2
[58] Field of Search .............. 252/174.17, 174.12, 252/DIG. 12, 125, DIG. 14; 536/4.1, 17.2

[56] References Cited

U.S. PATENT DOCUMENTS

| | | | |
|---|---|---|---|
| 3,729,461 | 4/1973 | Pomeranz | 260/210 |
| 3,737,426 | 6/1973 | Throckmorton et al. | 260/210 R |
| 3,931,148 | 1/1976 | Langdon et al. | 260/210 R |
| 4,011,169 | 3/1977 | Diehl et al. | 252/95 |
| 4,842,769 | 6/1989 | Shulman | 252/8.6 |
| 4,859,589 | 8/1989 | Godtfretsen et al. | 435/73 |
| 5,023,008 | 6/1991 | Scardera et al. | 252/106 |

FOREIGN PATENT DOCUMENTS

| | | |
|---|---|---|
| 005004 | 10/1979 | European Pat. Off. . |
| 0028866 | 5/1981 | European Pat. Off. . |
| 232851 | 8/1987 | European Pat. Off. . |
| 56-28296 | 3/1981 | Japan . |
| 59-053497 | 3/1984 | Japan . |
| 167237 | 3/1989 | Japan . |
| 1268616 | 10/1989 | Japan . |
| 4077493 | 3/1992 | Japan . |
| 2140818 | 5/1984 | United Kingdom . |

OTHER PUBLICATIONS

Kobayashi et al., J. Chem. Soc. Perkin. Trans. pp. 101–103 (1989).
Baruah et al., Phytochemistry, 22(8):1741–1744 (1983).
Williams et al., Archives of Biochemistry and Biophysics, 195(1):145–151 (1979).
Coulon-Moulec, Bull. Soc. Chem. Biol., 49(7):825–840 (1967).
Alvarez et al., J. Lipid Res., 31(6):1073–1081 (1990).

Primary Examiner—Paul Lieberman
Assistant Examiner—Kean Fries
Attorney, Agent, or Firm—Ronald A. Koatz

[57] ABSTRACT

The present invention relates to liquid detergent compositions wherein the detergent active mixture of the compositions comprises 65 to 99% of a glyceroglycolipid compound having an amine linkage and 1 to 35% of a nonionic surfactant. Unexpectedly, applicants have discovered a synergy in the mixture of these surfactants which leads to enhanced detergency.

2 Claims, 2 Drawing Sheets

COMPOSITIONS COMPRISING GLYCEROGLYCOLIPIDS HAVING AN AMINE LINKAGE AS A SURFACTANT OR COSURFACTANT

CROSS REFERENCES

This is a continuation-in-part of Ser. No. 07/816,423 filed Dec. 31, 1991.

BACKGROUND OF THE INVENTION

The present invention relates to detergent or personal product compositions comprising glyceroglycolipids having an amine linkage as surfactants or cosurfactants in the compositions. In particular, the glyceroglycolipid compounds are compounds having 1 to 4 saccharide units.

Natural glycolipids are known in the art and these structures have been elucidated. The term glycolipid refers to any of a class of lipids that, upon hydrolysis, yield a sugar (e.g., galactose or glucose), and a lipid (e.g. substituted glycerol group). One major class of these glycolipids belong to the glacier glycolipids, i.e., a glycolipids based around a glycerol frame structure. For example, the compound may have a sugar structure at one end of the glycerol structure instead of an —OH group and an ester linkage at one or both of the other —H groups that would normally be found on glycerol.

U.S. Pat. No. 3,729,461 to Pomeranz et al., for example, teaches mono- and di-galactosyl glyceride compounds isolated from wheat flour. On one end of the glycerol frame is found a sugar group (i.e., the mono- or di-saccharide group) and the two other OH groups normally found on a glycerol are esterified.

In Kobayashi et al., J. Chem Soc. Perkin., Trans. p. 101–103 (1989), there are again taught mono- and di-galactosyl diacylglycerols similar to those taught in Pomeranz et al. Again, there is a sugar group on one end and a mono- or diester where the remaining two —OH groups on a glycerol would normally be found.

Other ester functionalized mono- and diacyl galactosylglycerols are taught in Baruah et al., Phytochemistry, 22(8):1741–1744 (1983) and in U.S. Pat. No. 4,859,589 to Godfretsen et al.

Another example of a glyceroglycolipid is a compound having a sugar structure at one end of a glycerol structure instead of an —OH group and ether linkage on one or both of the other —OH groups that would normally be found on glycerol.

A glyceroglycolipid containing an ether linkage (where the —OH group on the glycerol would normally be found) is disclosed in Coulon-Moulec, Bull. Soc. Chem. Biol., 49(7):825–840 (1967); and in Alvarez et al., J. Lipid Res., 31(6):1073–1081 (1990).

These references are concerned, however, only with the synthesis of various lipid glycosides and contains absolutely no teaching or suggestion that glyceroglycolipids having an ether linkage can be used as surfactants or cosurfactants in detergent or personal product compositions.

EP No. 232,851-A (Assigned to National Starch) also appears to teach a glyceroglycolipid with an ether linkage. However, this reference is clearly concerned with compounds used as paper strength additives and neither teaches nor suggests that these compounds may be used as surfactants in detergent or personal wash compositions.

Other examples of glyceroglycolipids having an ether linkage are found in copending application filed on the same date as the present application.

William et al., Archives of Biochemistry and Biophysics, 195(1):145–151 (1979) teach certain alkyl bionamide compounds which are formed by linking aldobionic acids to an alkylamine through an amide bond. The compounds of the invention contain no such amide bond.

Scardera et al. (U.S. Pat. No. 5,023,008) teach a glycerol like frame structure with an amine group on one end. However, this structure has no sugar group on the other end.

Yet another example of a glyceroglycolipid might be a compound with a sugar group on one end of the glycerol structure instead of an —OH group and an amine group (i.e., $NRR^1$) at one or both of the other —OH groups normally found in glycerol, and in particular amines wherein one or both of R and $R^1$ are alkyl chains sufficient in length to confer surfactancy properties on the molecule.

U.S. Pat. No. 4,011,169 to Diehl et al., for example, teach enzyme containing compositions comprising certain aminated polysaccharides as stabilizing agents for enzymes. It is clear from this reference that the polysaccharides used have at the very least 5 or more saccharide units and, preferably, well over 100 (the application notes at column 7, lines 50–52, that natural polysaccharides smaller than this are rare). Further, there is a limitation to the amount of elemental nitrogen in the compound and it seems that compounds with fewer saccharide units would not meet this limitation.

U.S. Pat. No. 3,931,148 to Langdon teaches hydroxyalkylamino glycoside compounds which appear to be similar to those of the invention. However, there appears to be no teaching or suggestion that these compounds can be used in the specifically claimed detergent and personal product compositions of the invention.

Finally, because the compounds of the invention are derived from naturally occurring carbohydrates, the use of these compounds can provide a source of renewable raw materials that are synthetically versatile and environmentally friendly.

Accordingly, it is an object of this invention to provide novel surfactants and cosurfactants derived from carbohydrates and the use of such compounds in detergent and personal product compositions.

SUMMARY OF THE INVENTION

The present invention relates to glyceroglycolipid compounds having one or two amine linkage and to detergent and personal product compositions comprising these glyceroglycolipids for use as a surfactant or cosurfactant in the compositions. In particular the glyceroglycolipid has the following formula:

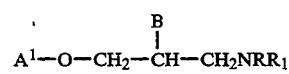

wherein $A^1$ is a saccharide, preferably having one to four saccharide units, more preferably a mono or disaccharide; R or $R_1$ are the same or different and can be hydrogen, a branched or unbranched, saturated or unsaturated hydrocarbon radical (including aryl, arene, etc.) having 1 to 24, preferably 6 to 18 carbons; and B is OH or a $NR_2R_3$ group wherein $R_2$ and $R_3$ are hydrogen or a branched or unbranched hydrocarbon radical having 1 to 24, preferably 6 to 18 carbons. It should be understood that the $NRR_1$ group and the B group are positionally interchangeable. It should also be understood that at least one of R, $R_1$, $R_2$ or $R_3$ must be a hydrocarbon radical (i.e., they may not all be hydrogen at the same time).

DETAILED DESCRIPTION OF THE INVENTION

Figure 1:
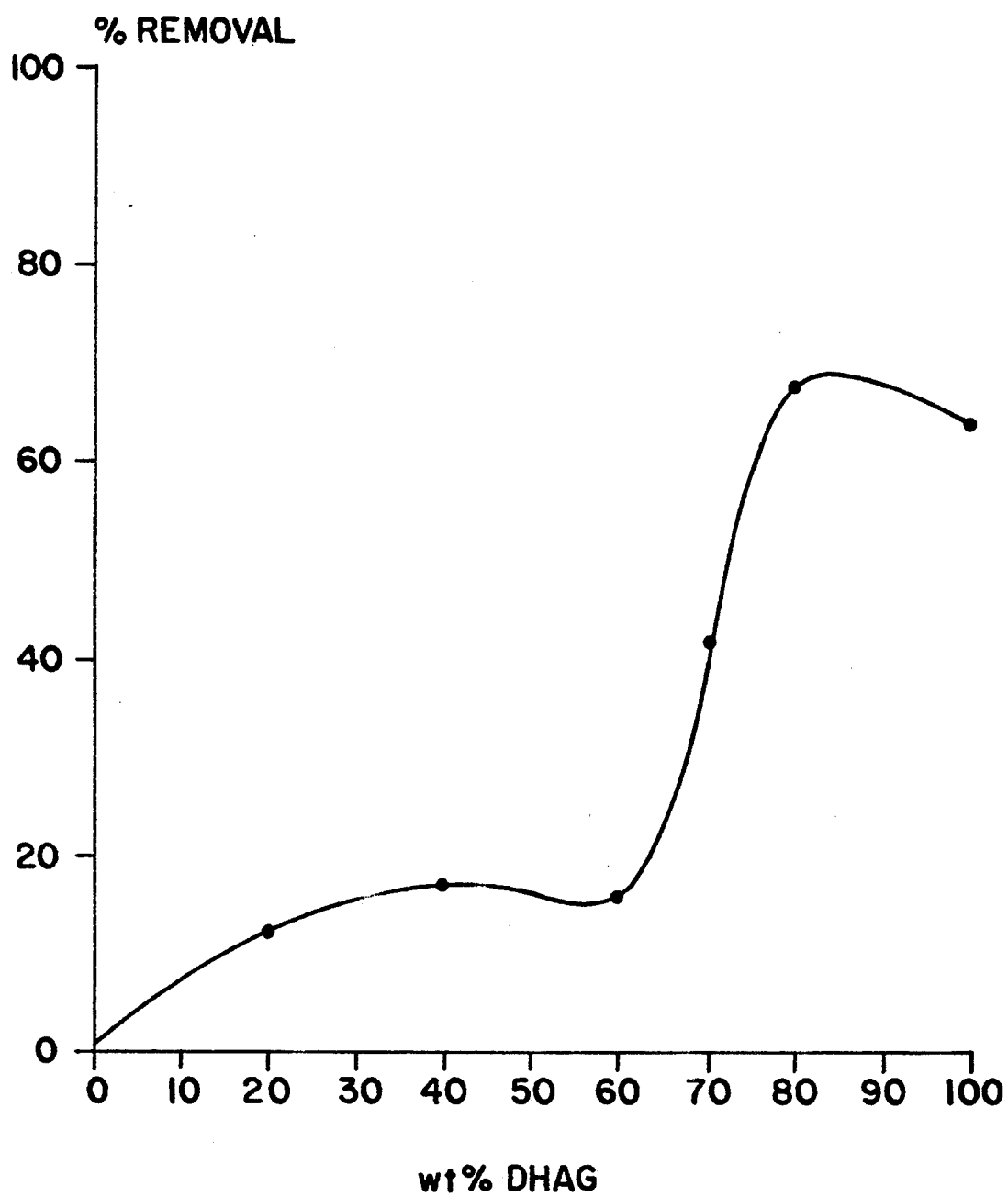
FIG. 1—Graph of the removal of an oily detergent (triolein) from polyester using varying ratios of DHAG and $C_{12}EO_3$ in a carbonate buffered solution.

The present invention provides detergent and personal product compositions comprising, as a surfactant or cosurfactant, a glyceroglycolipid compound having the structure set forth below:

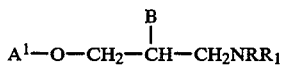

wherein $A^1$ is a saccharide, preferably having one or more saccharide units, more preferably a mono- or disaccharide, and most preferably a monosaccharide such as glucose or galactose;

R or $R_1$ are same or different and are hydrogen, a branched or unbranched hydrocarbon radical (including aryl, arene, etc.) having from about 1 to about 24, preferably from about 6 to about 18 carbons; and B is OH or a $NR_2R_3$ group, wherein $R_2$ and $R_3$ may be the same or different and are hydrogen, a branched or unbranched hydrocarbon radical having 1 to 24, preferably from 6 to 18 carbons; and $NRR_1$ and B are positionally interchangeable.

It should also be understood that at least one of R, $R_1$, $R_2$ or $R_3$ must be a hydrocarbon radical (i.e., not all may be hydrogen at the same time) in order to ensure that surfactancy behavior is given to the compound. Preferably, at least one of these groups should be $C_6-C_{22}$, most preferably $C_{10}-C_{14}$.

Preferably the compound is a monoalkylamine such that R (or $R_1$) is hydrogen and $R_1$ (or R) is an alkyl chain having, for example, 10 to 14 carbons.

In a preferred embodiment of the invention, $A^1$ is a monosaccharide and, in particular, is a galactoside (e.g., D-galactoside), R is a $C_{12}$ alkyl chain, $R_1$ is hydrogen and B is OH.

Other examples of compounds of the invention (having varying $NRR^1$ or $A^1$ groups) are set forth below:

3-(butylamino)-2-hydroxypropyl-β-D-Galactopyranoside
3-(pentylamino)-2-hydroxypropyl-β-D-Galactopyranoside
3-(hexylamino)-2-hydroxypropyl-β-D-Galactopyranoside
3-(heptylamino)-2-hydroxypropyl-β-D-Galactopyranoside
3-(octylamino)-2-hydroxypropyl-β-D-Galactopyranoside
3-(nonylamino)-2-hydroxypropyl-β-D-Galactopyranoside
3-(decylamino)-2-hydroxypropyl-β-D-Galactopyranoside
3-(dodecylamino)-2-hydroxypropyl-β-D-Galactopyranoside
3-(tetradecylamino)-2-hydroxypropyl-β-D-Galactopyranoside
3-(hexadecylamino)-2-hydroxypropyl-β-D-Galactopyranoside
3-(octadecylamino)-2-hydroxypropyl-β-D-Galactopyranoside
3-(eicosylamino)-2-hydroxypropyl-β-D-Galactopyranoside
3-(docosylamino)-2-hydroxypropyl-β-D-Galactopyranoside
3-(tetracosylamino)-2-hydroxypropyl-β-D-Galactopyranoside
3-(hexenylamino)-2-hydroxypropyl-β-D-Galactopyranoside
3-(decenylamino)-2-hydroxypropyl-β-D-Galactopyranoside
3-(dodecenylamino)-2-hydroxypropyl-β-D-Galactopyranoside
3-(tetradecenylamino)-2-hydroxypropyl-β-D-Galactopyranoside
3-(hexadecenylamino)-2-hydroxypropyl-β-D-Galactopyranoside
3-(octadecenylamino)-2-hydroxypropyl-β-D-Galactopyranoside
3-(docosenylamino)-2-hydroxypropyl-β-D-Galactopyranoside
3-(tetracosenylamino)-2-hydroxypropyl-β-D-Galactopyranoside
3-(3-oxa-tridecylamino)-2-hydroxypropyl-β-D-Galactopyranoside
3-(fluorododecylamino)-2-hydroxypropyl-β-D-Galactopyranoside
3-(butylamino)-2-hydroxypropyl-β-D-Glucopyranoside
3-(pentylamino)-2-hydroxypropyl-β-D-Mannopyranoside
3-(tetradecyloxy)-2-hydroxypropyl-β-D-lactoside
3-(octadecyloxy)-2-hydroxypropyl-β-D-maltoside
3-(octyloxy)-2-hydroxypropyl-β-D-galactotrioside
3-(dodecyloxy)-2-hydroxypropyl-βD-cellotrioside

SYNTHESIS

The glyceroglycolipid of the invention is formed from a precursor having an epoxide group at the location where the amine linkage is formed and having a sugar group. The sugar may be protected or unprotected. An example of such a precursor would be the β-D-galactose epoxide compound having the structure:

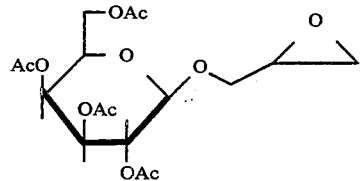

Once the protected epoxide galactose compound is obtained, this can be reacted with a primary or secondary amine $NH_2R$ or $NHRR_1$ (wherein R and $R_1$ represents the desired chain length of the alkyl groups forming the amine linkage). The amine is added in an inert solvent (e.g. tetrahydrofuran, acetonitrile, dioxane) or neat.

The epoxide precursor used to form the desired surfactant can in turn be formed in a variety of ways.

For example, a galactose epoxide compound may be synthesized enzymatically via the hydrolysis of lactose in the presence of allyl alcohol and β-galactosidase to form a allyl-β-D-galactopyranoside which can then be protected and oxidized to the corresponding epoxide with m-chloroperoxybenzoic acid (m-CPBA) in dichloromethane.

This type of reaction, which is taught in Nilsson, K. G. I., *Carbohydrate Research*, 180:53–59 (1988) is set forth below:

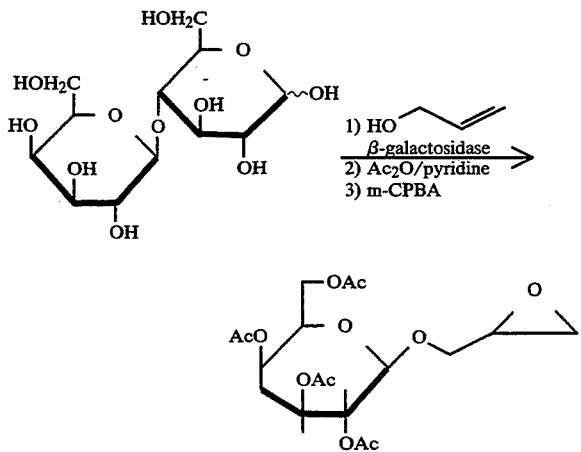

A chemical mode for preparation of the galactose epoxide involves the use of acetobromogalactose (2,3,4,6-tetra-O-acetyl-α-D-galactopyranosyl bromide) mixed with allyl alcohol and mercuric cyanide. This simple Koenigs-Knorr glycosydation affords the allyl-β-D-galactopyranoside tetraacetate in very good yield. Oxidation with peracide gives the protected epoxide sugar.

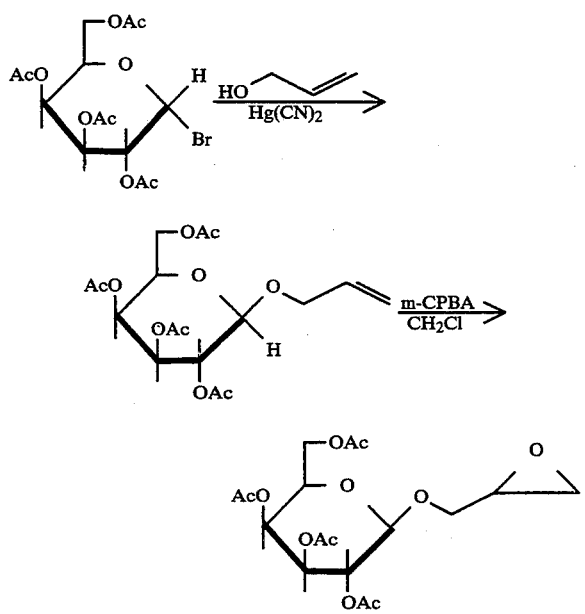

Once the epoxide precursor is formed, the epoxide is opened with an amine with formation of the amine bond and one free hydroxy group.

COMPOSITIONS

The surfactants of the invention may be used in cleansing or detergent composition such as heavy duty liquid detergents (generally enzyme containing) or powdered detergents. Examples of liquid or powdered detergents are described in U.S. Pat. No. 4,959,179 to Aronson (for liquid detergent compositions) and U.S. Pat. No. 4,929,379 to Oldenburg et al. (for powdered detergent compositions), both of which are incorporated herein by reference.

The liquid detergent compositions of the invention may be built or unbuilt and may be aqueous or nonaqueous. The compositions generally comprise about 5%–70% by weight of a detergent active material and from 0% to 50% of a builder. The composition may comprise 5–70% entirely the surfactant of the invention or it may comprise a mixture of surfactants wherein the surfactant of the invention comprises 60 to 99% of the mixture, preferably 75 to 90% of the mixture.

The liquid detergent compositions of the invention may further comprise an amount of electrolyte (defined as any water-soluble salt) whose quantity depends on whether or not the composition is structured. By structured is meant the formation of a lamellar phase sufficient to endow solid suspending capability.

More particularly, while no electrolyte is required for a non-structured, non-suspending composition, at least 1%, more preferably at least 5% by weight and most preferably at least 15% by weight electrolyte is used. The formation of a lamellar phase can be detected by means well known to those skilled in the art.

The water-soluble electrolyte salt may be a detergency builder, such as the inorganic salt sodium tripolyphosphate or it may be a non-functional electrolyte such as sodium sulphate or chloride. Preferably, whatever builder is used in the composition comprises all or part of the electrolyte.

The liquid detergent composition generally further comprises enzymes such as proteases, lipases, amylases and cellulases which, when present, may be used in amounts from about 0.01 to 5% of the compositions. Stabilizers or stabilizer systems may be used in conjunction with enzymes and generally comprise from about 0.1 to 15% by weight of the composition.

The enzyme stabilization system may comprise calcium ion; boric acid, propylene glycol and/or short chain carboxylic acids. The composition preferably contains from about 0.01 to about 50, preferably from about 0.1 to about 30, more preferably from about 1 to about 20 millimoles of calcium ion per liter.

When calcium ion is used, the level of calcium ion should be selected so that there is always some minimum level available for the enzyme after allowing for complexation with builders, etc., in the composition. Any water-soluble calcium salt can be used as the source of calcium ion, including calcium chloride, calcium formate, calcium acetate and calcium propionate. A small amount of calcium ion, generally from about 0.05 to about 2.5 millimoles per liter, is often also present in the composition due to calcium in the enzyme slurry and formula water.

Another enzyme stabilizer which may be used is propionic acid or a propionic acid salt capable of forming propionic acid. When used, this stabilizer may be used in an amount from about 0.1% to about 15% by weight of the composition.

Another preferred enzyme stabilizer is polyols containing only carbon, hydrogen and oxygen atoms. They preferably contain from 2 to 6 carbon atoms and from 2 to 6 hydroxy groups. Examples include propylene glycol (especially 1,2 propanediol which is preferred), ethylene glycol, glycerol, sorbitol, mannitol and glucose. The polyol generally represents from about 0.5% to about 15%, preferably from about 1.0% to about 8% by weight of the composition.

The composition herein may also optionally contain from about 0.25% to about 5%, most preferably from about 0.5% to abount 3% by weight of boric acid. The boric acid may be, but is preferably not, formed by a compound capable of forming boric acid in the composition. Boric acid is preferred, although other compounds such as boric oxide, borax and other alkali metal borates (e.g. sodium ortho-, meta- and pyroborate and sodium pentaborate) are suitable. Substituted boric acids (e.g., phenylboronic acid, butane boronic acid and a p-bromo phenylboronic acid) can also be used in place of boric acid.

On especially preferred stabilization system is a polyol in combination with boric acid. Preferably, the weight ratio of polyol to boric acid added is at least 1, more preferably at least about 1.3.

With regard to the detergent active, the detergent active material may be an alkali metal or alkanolamine soap or a 10 to 24 carbon atom fatty acid, including polymerized fatty acids, or an anionic, a nonionic, cationic, zwitterionic or amphoteric synthetic detergent material, or mixtures of any of these.

Examples of the anionic synthetic detergents are salts (including sodium, potassium, ammonium and substituted ammonium salts) such as mono-, di- and triethanolamine salts of 9 to 20 carbon alkylbenzenesulphonates, 8 to 22 carbon primary or secondary alkanesulphonates, 8 to 24 carbon olefinsulphonates sulphonated polycarboxylic acids prepared by sulphonation of pyrolyzed product of alkaline earth metal citrates, e.g., as described in British Patent specification, 1,082,179, 8 to 22 carbon alkylsulphates, 8 to 24 carbon alkylpolyglycol-ether-sulphates, -carboxylates and -phosphates (containing up to 10 moles of ethylene oxide); further examples are described in "Surface Active Agents and Detergents" (vol. I and II) by Schwartz, Ferry and Bergh. Any suitable anionic may be used and the examples are not intended to be limiting in any way.

Examples of nonionic synthetic detergents which may be used with the invention are the condensation products of ethylene oxide, propylene oxide and/or battalion oxide with 8 to 18 carbon alkylphenols, 8 to 18 carbon fatty acid amides; further examples of nonionics include tertiary amine oxides with 8 to 18 carbon alkyl chain and two 1 to 3 carbon alkyl chains. The above reference also describes further examples of nonionics.

The average number of moles of ethylene oxide and/or propylene oxide present in the above nonionics varies from 1–30; mixtures of various nonionics, including mixtures of nonionics with a lower and a higher degree of alkoxylation, may also be used.

The nonionic may also be a sugar amide such as a polysaccharide amide. Specifically, the surfactant may be one of the lactobionamides described in U.S. Ser. No. 816,419 to Au et al., hereby incorporated by reference, or it may be a polyhydroxide amide such as, for example, those described in U.S. Pat. No. 5,009,814 to Kelkenberg, hereby incorporated by reference in the subject application.

Examples of cationic detergents which may be used are the quaternary ammonium compounds such as alkyldimethylammonium halogenides.

Examples of amphoteric or zwitterionic detergents which may be used with the invention are N-alkylamine acids, sulphobetaines, condensation products of fatty acids with protein hydrolysates; but owing to their relatively high costs they are usually used in combination with an anionic or a nonionic detergent. Mixtures of the various types of active detergents may also be used, and preference is given to mixtures of an anionic and a nonionic detergent active. Soaps (in the form of their sodium, potassium and substituted ammonium salts) of fatty acids may also be used, preferably in conjunction with an anionic and/or nonionic synthetic detergent.

Builders which can be used according to this invention include conventional alkaline detergency builders, inorganic or organic, which can be used at levels from 0% to about 50% by weight of the composition, preferably from 1% to about 20% by weight, most preferably from 2% to about 8%.

Examples of suitable inorganic alkaline detergency builders are water-soluble alkalimetal phosphates, polyphosphates, borates, silicates and also carbonates. Specific examples of such salts are sodium and potassium triphosphates, pyrophosphates, orthophosphates, hexametaphosphates, tetraborates, silicates and carbonates.

Examples of suitable organic alkaline detergency builder salts are: (1) water-soluble amino polycarboxylates, e.g., sodium and potassium ethylenediaminetetraacetates, nitrilotriacetates and N-(2 hydroxyethyl)-nitrilodiacetates; (2) water-soluble salts of phytic acid, e.g., sodium and potassium phytates (see U.S. Pat. No. 2,379,942); (3) water-soluble polyphosphonates, including specifically, sodium, potassium and lithium salts of ethane-1-hydroxy-1,1-diphosphonic acid; sodium, potassium and lithium salts of methylene diphosphonic acid; and sodium, potassium and lithium salts of ethane-1,1,2-triphosphonic acid. Other examples include the alkali methal salts of ethane-2-carboxy-1,1-diphosphonic acid hydroxymethanediphosphonic acid, carboxylidiphosphonic acid, ethane-1-hydroxy-1,1,2-triphosphonic acid, ethane-2-hydroxy-1,1,2-triphosphonic acid, propane-1,1,3,3-tetraphosphonic acid, propane-1,1,2,3-tetraphosphonic acid, and propane-1,2,2,3-tetraphosphonic acid; (4) water soluble salts of polycarboxylate polymers and copolymers as described in U.S. Pat. No. 3,308,067.

In addition, polycarboxylate builders can be used satisfactorily, including water-soluble salts of mellitic acid, citric acid, and carboxymethyloxysuccinic acid and salts of polymers of itaconic acid and maleic acid. Other polycarboxylate builders include DPA (dipicolinic acid) and ODS (oxydisuccinic acid). Certain zeolites or aluminosilicates can be used. One such aluminosilicate which is useful in the compositions of the invention is an amorphous water-insoluble hydrated compound of the formula $Na_x(_yAlO_2.SiO_2)$, wherein x is a number from 1.0 to 1.2 and y is 1, said amorphous material being further characterized by a Mg++ exchange capacity of from about 50 mg eq. $CaCO_3$/g. and a particle diameter of from about 0.01 micron to about 5 microns. This ion exchange builder is more fully described in British Pat. No. 1,470,250.

A second water-insoluble synthetic aluminosilicate ion exchange material useful herein is crystalline in nature and has the formula $Na_z[(AlO_2)_y.(SiO_2)]xH_2O$, wherein z and y are integers of at least 6; the molar ratio of z and y is in the range from 1.0 to about 0.5, and x is an integer from about 15 to about 264; said aluminosilicate ion exchange material having a particle size diameter from about 0.1 micron to about 100 microns; a calcium ion exchange capacity on an anhydrous basis of at least about 200 milligrams equivalent of $CaCO_3$ hardness per gram; and a calcium exchange rate on an anhydrous basis of at least about 2 grams/gallon/minute/gram. These synthetic aluminosilicates are more fully described in British Pat. No. 1,429,143.

In addition to the ingredients described hereinbefore, the preferred compositions herein frequently contain a series of optional ingredients which are used for the known functionality in conventional levels. While the detergent compositions are generally premised on aqueous, enzyme-containing detergent compositions, it is frequently desirable to use a phase regulant. This component together with water constitutes then the solvent matrix for the claimed liquid compositions. Suitable phase regulants are well-known in liquid detergent technology and, for example, can be represented by hydrotropes such as salts of alkylarylsulfonates having up to 3 carbon atoms in the alkylgroup, e.g., sodium, potassium, ammonium and ethanolamine salts of xylene-, toluene-, ethylbenzene-, cumene-, and isopropylbenzene sulfonic acids. Alcohols may also be used as phase regulants. This phase regulant is frequently used in an amount from about 0.5% to about 20%, the sum of phase regulant and water is normally in the range from 35% to 65%.

The preferred compositions herein can contain a series of further optional ingredients which are mostly used in additive levels, usually below about 5%. Examples of the like additives include: polyacids, suds regulants, opacifiers, antioxidants, bactericides, dyes, perfumes, brighteners and the like.

The beneficial utilization of the claimed compositions under various usage conditions can require the utilization of a suds regulant. While generally all detergent suds regulants can be utilized, preferred for use herein are alkylated polysiloxanes such as dimethylpolysiloxane, also frequently termed silicones. The silicones are frequently used in a level not exceeding 0.5%, most preferably between 0.01% and 0.2%.

It can also be desirable to utilize opacifiers inasmuch as they contribute to create a uniform appearance of the concentrated liquid detergent compositions. Examples of suitable opacifiers include: polystyrene commercially known as LYTRON 621 manufactured by Monsanto Chemical Corporation. The opacifiers are frequently used in an amount from 0.3% to 1.5%.

The compositions herein can also contain known antioxidants for their known utility, frequently radical scavengers in the art established levels, i.e., 0.001% to 0.25% (by reference to total composition). These antioxidants are frequently introduced in conjunction with fatty acids.

The liquid detergent compositions of the invention may also contain deflocculating polymers such as described in U.S. Ser. No. 664,513, filed Mar. 5, 1991, hereby incorporated by reference.

When the liquid composition is an aqueous composition, the balance of the formulation consists of an aqueous medium. When it is in the form of a non-aqueous composition, the above ingredients make up for the whole formulation (a non-aqueous composition may contain up to about 5% water).

An ideal liquid detergent composition might contain (all percentages by weight):
(1) 5–70% detergent active system;
(2) 0–50% builder;
(3) 0–40% electrolyte
(4) 0.01–5% enzyme;
(5) 0.1–15% enzyme stabilizer;
(6) 0–20% phase regulant; and
(7) remainder water and minors The detergent composition of the invention might also be a powdered detergent composition.

Such powdered compositions generally comprise from about 5–40% of a detergent active system which generally consists of an anionic, a nonionic active, a fatty acid soap or mixtures thereof; from 20–70% of an alkaline buffering agent; up to about 40% builder and balance minors and water.

The alkaline buffering agent may be any such agent capable of providing a 1% product solution with a DH of above 11.5 or even 12. Advantageous alkaline buffering agents are the alkalimetal silicates, as they decrease the corrosion of metal parts in washing machines, and in particular sodium orthometa- or di-silicates, of which sodium metasilicate is preferred. The alkaline buffering agent is present in an amount of from 0 to 70% by weight, preferably from 0 to 30% by weight.

In addition the compositions of the invention can and normally will contain detergency builders in an amount of up to 40% by weight and preferably from 5 to 25% by weight of the total composition.

Suitable builders include sodium, potassium and ammonium or substituted ammonium pyro- and tri-polyphosphates, -ethylene diamine tetraacetates, -nitrilotriacetates, -etherpolycarboxylates, -citrates, -carbonates, -orthophosphates, -carboxymethyloxysuccinates, etc. Other builders include DPA and ODS. Also less soluble builders may be included, such as e.g., an easily dispersible zeolite. Particularly preferred are the polyphosphate builder salts, nitrilotriacetates, citrates, carboxymethyloxysuccinates and mixtures thereof.

Other conventional materials may be present in minor amounts, provided they exhibit a good dissolving or dispersing behavior; for example sequestering agents, such as ethylenediamine tetraphosphonic acid; soil-suspending agents, such as sodiumcarboxymethylcellulose, polyvinylpyrrolidone or the maleic anhydride/vinylmethylether copolymer, hydrotropes; dyes; perfumes; optical brighteners; alkali-stable enzymes; germicides; anti-tarnishing agents; lather depressants; fabric softening agents; oxygen- or chlorine-liberating bleaches, such as dichlorocyanuric acid salts or alkalimetal hypochlorides.

The remainder of the composition is water.

An ideal powdered detergent composition might contain the following (all percentages by weight):
(1) 5–40% detergent active system;
(2) 0–40% builder;
(3) 0–30% buffer salt;
(4) 0–30% sulfate;
(5) 0–20% bleach system;
(6) 0–4% enzyme;
(7) minors plus water to 100%.

The surfactants of the invention may also be used in personal product compositions such as, for example, soap bar compositions, facial or body cleansing compositions, shampoos for hair or body, conditioners, cosmetic compositions or dental compositions.

In one embodiment of the invention, the surfactant of the invention may be used, for example, in a toilet bar (i.e. soap and/or detergent bar) formulation.

Typical toilet bar compositions are those comprising fatty acid soaps used in combination with a detergent other than fatty acid soap and free fatty acids. It should be noted that the composition may comprise no fatty acid soap and may be based on actives other than fatty acid soap. Mildness improving salts, such as alkali metal salt or isethionate, are also typically added. In addition other ingredients, such as germicides, perfumes, colorants, pigments, suds-boosting salts and anti-mushing agents may also be added.

Fatty acid soaps are typically alkali metal or alkanol ammonium salts of aliphatic alkane or alkene monocarboxylic acids. Sodium, potassium, mono-, di- and triethanol ammonium cations, or combinations thereof, are suitable for purposes of the invention. The soaps are well known alkali metal salts of natural or synthetic aliphatic (alkanoic or alkenoic) acids having about 8 to 22 carbons, preferably 12 to about 18 carbons.

Examples of soap which may be used may be found in U.S. Pat. No. 4,695,395 to Caswell et al. and U.S. Pat. No. 4,260,507 (Barrett), both of which are incorporated herein by reference.

In a soap-based bar, fatty acid soaps will generally comprise greater than 25% of the composition, generally from 30-95%. Preferably, the amount of soap will range from 40% to 70% by weight of the composition.

In a bar based on other actives, soap may comprise 0-50% by weight. In general $C_8$ to $C_{24}$ fatty acid comprises 5-60% of the composition.

The compositions will also generally comprise a non-soap detergent which is generally chosen from anionic, nonionic, cationic, zwitterionic or amphoteric synthetic detergent materials or mixtures thereof. These surfactants are all well known in the art and are described, for example, in U.S. Pat. Nos. 4,695,395 and 4,260,507 discussed above. One preferred non-soap anionic is a $C_8$–$C_{22}$ akyl isethionate. These ester may be prepared by the reaction between alkali metal isethionate and mixed aliphatic fatty acids having from 8 to 22 carbons. The non-soap actives may comprise from 0 to 50% of the composition.

A certain amount of free fatty acids of 8 to 22 carbons are also desirably incorporated into soap compositions to act as superfatting agents or as skin feel and creaminess enhancers. If present, the free fatty acids comprise between 1 and 15% of the compositions.

A preferred mildness improving salt which may be added to soap compositions is a simple unsubstituted sodium isethionate. This may be present as 0.1 to 50% of the composition, preferably 0.5% to 25%, more preferably 2% to about 15% by weight. Other mildness co-actives which may be used include betain compounds or ether sulphates. These also may be present at 0.1 to 50% of the composition, preferably 0.5% to 25%.

The sulfate ester surfactant may comprise 0.01 to 45% by weight of the composition (as the monoester), preferably 25% to 40%, and 0.01% to 10% of the composition (as the diester), preferably 0.01% to 5%.

Other optional ingredients which may be present in soap bar compositions are moisturizers such as glycerin, propylene glycol, sorbitol, polyethylene glycol, ethoxylated or methoxylated ether of methyl glucose etc; water-soluble polymers such as collagens, modified cellulases (such as Polymer JR(®)), guar gums and polyacrylates; sequestering agents such as citrate, and emollients such as silicones or mineral oil. Another useful set of ingredients are various cosurfactants and non-soap detergents.

In a second embodiment of the invention, the glycerol frame surfactant with ether linkage of the invention may be present in a facial or body cleansing composition. Examples of such cleaning compositions are described, for example, in U.S. Pat. No. 4,812,253 to Small et al. and U.S. Pat. No. 4,526,710 to Fujisawa, both of which are hereby incorporated by reference.

Typically, cleansing compositions will comprise a fatty acid soap together with a non-soap surfactant, preferably a mild synthetic surfactant. Cleaning compositions will also generally include a moisturizer or emollient and polymeric skin feel and mildness aids. The compositions may further optionally include thickener (e.g. magnesium aluminum silicate, carbopol), conditioners, water soluble polymers (e.g. carboxymethyl cellulose), dyes, hydrotropes brighteners, perfumes and germicides.

The fatty acid soaps used are such as those described above in uses in detergent bar formulations. These soaps are typically alkali metal or alkanol ammonium salts of aliphatic or alkene monocarboxylic salts. Sodium, potassium, mono-, di- and triethanol ammonium cations, or combinations thereof are suitable. Preferred soaps are 8 to 24 carbon half acid salts of, for example, triethanolamine.

Surfactants can be chosen from anionic, nonionic, cationic, zwitterionic or amphoteric materials or mixtures thereof such as are described in U.S. Pat. No. 4,695,395 mentioned above, or in U.S. Pat. No. 4,854,333 to Inman et al, hereby incorporated by reference.

Moisturizers are included to provide skin conditioning benefits and improve mildness. This term is often used as synonymous with emollient and is then used to describe a material which imparts a smooth and soft feeling to skin surface.

There are two ways of reducing water loss from the stratum corneum. One is to deposit on the surface of the skin an occlusive layer which reduces the rate of evaporation. The second method is to add nonocclusive hydgroscopic substances to the stratum corneum which will retain water, and make this water available to the stratum corneum to alter its physical properties and produce a cosmetically desirable effect. Nonocclusive moisturizers also function by improving the lubricity of the skin.

Both occlusive and nonocclusive moisturizers can work in the present invention. Some examples of moisturizers are long chain fatty acids, liquid water-soluble polyols, glycerin, propylene glycol, sorbitol, polyethylene glycol, ethoxylated/propoxylated ethers of methyl glucose (eg., methyl gluceth-20) and ethoxylated/propoxylated ethers of lanolin alcohol (e.g., Solulan-75).

Preferred moisturizers are coco and tallow fatty acids. Some other preferred moisturizers are the nonoclusive liquid water soluble polyols and the essential amino acid compounds found naturally in the skin.

Other preferred nonocclusive moisturizers are compounds found to be naturally occurring in the stratum corneum of the skin, such as sodium pyrrolidone carboxylic acid, lactic acid, urea, L-proline, guanidine and pyrrolidone. Examples of other nonocclusive moisturizers include hexadecyl, myristyl, isodecyl or isopropyl esters of adipic, lactic, oleic, stearic, isostearic, myristic or linoleic acids, as well as many of their corresponding alcohol esters (sodium isostearoyl-2 lactylate, sodium capryl lactylate), hydrolyzed protein and other collagen-derived proteins, aloe vera gel and acetamide MEA.

Some occlusive moisturizers include petrolatum, mineral oil, beeswax, silicones, lanolin and oil-soluble lanolin derivatives, saturated and unsaturated fatty alcohols such as behenyl alcohol, squalene and squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Other examples of both types of moisturizers are disclosed in "Emollients—a Critical Evaluation," by J. Mausner, Cosmetics & Toiletries, May, 1981, incorporated herein by reference.

The polymeric skin feel and mildness aids useful in the present invention are the cationic, anionic, amphoteric, and the nonionic polymers used in the cosmetic field. Reduced skin irritation benefits as measured by patch testing of cationic and nonionic types of polymers are set out in "Polymer JR for Skin Care" Bulletin, by Union Carbide, 1977. The cationics are preferred over the others because they provide better skin feel benefits.

The amount of polymeric skin feel and mildness aids found useful in the composition of the present invention is from about 0.01% to about 5%, preferably from about 0.3% to about 4%. In bar compositions with less than 5.5% soap, the polymer is used at a level of 2% to 5%, preferably 3% or more.

Other types of high molecular weight polymeric skin feel and skin mildness aids, such as nonionic guar gums, Merquats 100 and 550, made by Merck & Co, Inc.; Jaguar C-14-S made by Stein Hall; Mirapol a15 made by Miranol Chemical Company, Inc.; and Galactasol 811, made by Henkel, Inc.; plus others, are usable. The polymer also provides enhanced creamy lather benefits.

The nonionic polymers found to be useful include the nonionic polysaccharides, e.g., nonionic hydroxypropyl guar gums, offered by Celanese Corp. A preferred nonionic hydroxypropyl guar gum material is Jaguar ® R HP-60 having molar substitution of about 0.6. Another class of useful nonionics is the cellulosic nonionic polymers, e.g., HEC and CMC.

The cationic polymers employed in this invention also provide a desirable silky, soft, smooth in-use feeling. The preferred level for this invention is 0.1-5% of the composition. There is reason to believe that the positively charged cationic polymers can bind with negatively charges sites on the skin to provide a soft skin feel after use. Not to be bound by any theory, it is believed that the greater the charge density of the cationic polymer, the more effective it is for skin feel benefits.

Other suitable cationic polymers are copolymers of dimethylaminoethylmethacrylate and acrylamide and copolymers of dimethyldiallylammonium chloride and acrylamide in which the ratio of the cationic to neutral monomer units has been selected to give a copolymer having a cationic charge. Yet other suitable types of cationic polymers are the cationic starches, e.g., Sta-Lok ® 300 and 400 made by Staley, Inc.

A more complete list of cationic polymers useful in the present invention is described in U.S. Pat. No. 4,438,095, to Grollier/allec, issued Mar. 20, 1984, incorporated herein by reference. Some of the more preferred cationics are listed in Col. 3, Section 2; Col. 5, section 8; Col. 8, section 10; and Col. 9, lines 10–15 of the Grollier/allec patent, incorporated herein by reference.

In a third embodiment of the invention, the surfactant of the invention may be used, for example, in a shampoo. Examples of such compositions are described in U.S. Pat. No. 4,854,333, to Inman and U.S. Pat. No. 4,526,710 to Fujisawa, both of which are hereby incorporated by reference.

The shampoo compositions which may be used typically comprise a surfactant selected from any one of a wide variety of surfactants known in the art (such as those described in U.S. Pat. No. 4,854,333, incorporated herein by reference). The shampoo compositions may additionally comprise a compound considered useful for treating dandruff, e.g. selenium sulfide.

The compositions all may also optionally comprise a suspending agent, for example, any of several acyl derivative materials or mixtures thereof. Among these are ethylene glycol esters of fatty acids having 16 to 22 carbons. Preferred suspending agents include ethylene glycol stearates, both mono- and distearate. Preferred alkanol amides are stearic monoethanolamide, stearic diethanolamide and stearic monoisopropanolamide. Still other long chain acyl derivatives include long chain esters of long chain fatty acids (e.g., stearyl stearate, cetyl palmitate), glyceryl esters (e.g. glyceryl distearate), and long chain esters of long chain alkanol amides (e.g., stearamide DEA distearate, stearamide MEA stearate).

Still other suitable suspending agents are alkyl (16 to 22 carbon) dimethyl amine oxides, such as stearyl dimethyl amine oxide. If the compositions contain an amine oxide or a long chain acyl derivative as a surfactant, these components may also provide the suspending function and additional suspending agent may not be needed.

Xanthan gum is another agent used to suspend, for example, selenium sulfide which may be in the present compositions. This biosynthetic gum material is commercially available and is a heteropolysaccharide with a molecular weight of greater than 1 million. It is believed to contain D-glucose, D-mannose and D-glucuronate in the molar ratio of 2.8:2.0:2.0. The polysaccharide is partially acetylated with 4.7% acetyl. Supplemental information on these agents is found in Whistler, Roy L. (Editor), *Industrial Gums—Polysaccharides and Their Derivatives* New York: Academic Press, 1973. Kelco, a Division of Merck & Co., Inc., offers xanthan gum as Keltrol ®.

A particularly preferred suspending system comprises a mixture of xanthan gum, present at a level of from about 0.05% to about 1.0%, preferably from about 0.2% to about 0.4%, of the compositions, together with magnesium aluminum silicate ($Al_2Mg_8Si_2$), present at a level of from about 0.1% to about 3.0%, preferably from about 0.5% to about 2.0%, of the compositions. Magnesium aluminum silicate occurs naturally in such smectite minerals as colerainite, saponite and sapphire. Refined magnesium aluminum silicates useful herein are readily available, for example as veegum, manufactured by R.T. Vanderbilt Company, Inc. Mixtures of suspending agents are also suitable for use in the compositions of this invention.

Other useful thickening agents are the cross-linked polyacrylates such as those manufactured by B. F. Goodrich and sold under the Carbopol(®) tradename.

Another optional component for use in the present compositions is an amide. The amide used in the present compositions can be any of the alkanolamides of fatty acids known for use in shampoos. These are generally mono- and diethanolamides of fatty acids having from about 8 to 24 carbon atoms. Preferred are coconut monoethanolamide, lauric diethanolamide and mixtures thereof. The amide is present at a level of from about 1% to about 10% of the compositions.

The compositions may also contain nonionic polymer material which is used at a low level to aid in dispersing particles. The material can be any of a large variety of types including cellulosic materials such as hydroxypropyl methyl cellulose, carboxymethyl cellulose, hydroxyethyl cellulose and sodium carboxymethyl cellulose as well as mixtures of these materials.

Other materials include alginates, polyacrylic acids, polyethylene glycol and starches, among many others. The nonionic polymers are discussed in detail in *Industrial Gums*, edited by Roy L. Whistler, academic Press, Inc., 1973, and *Handbook of Water-Soluble Gums and Resins*, edited by Robert L. Davidson, McGraw-Hill, Inc., 1980. Both of these books in their entirety are incorporated herein by reference.

When included, the nonionic polymer is used at a level of from about 0.001% to about 0.1%, preferably from about 0.002% to about 0.05%, of the composition. Hydroxypropyl methyl cellulose is the preferred polymer.

Another suitable optional component useful in the present compositions is a nonvolatile silicone fluid.

The nonvolatile silicone fluid may be either a polyalkyl siloxane, a polyaryl siloxane, a polyalkylarly siloxane or a polyether siloxane copolymer and is present at a level of from about 0.1% to about 10.0%, preferably from about 0.5% to about 5.0%. Mixtures of these fluids may also be used and are preferred in certain executions. The dispersed silicone particles should also be insoluble in the shampoo metrix. This is the meaning of "insoluble" as used herein.

The essentially nonvolatile polyalkyl siloxane fluids that may be used include, for example, polydimethyl siloxanes with viscosities ranging from about 5 to about 600,000 centistokes at 25° C. These siloxanes are available, for example, from the General Electric Company as the Viscasil series and from Dow Corning as the Dow Corning 200 series. The siloxane viscosity can be measured by means of a glass capillary viscometer as set forth in Dow Corning Corporate Test Method CTM0004, Jul. 20, 1970. Preferably the viscosity of the these siloxanes range from about 350 centistokes to about 100,000 centistokes.

The essentially nonvolatile polyether siloxane copolymer that may be used is, for example, a polypropylene oxide modified dimethylpolysiloxane (e.g., Dow Corning DC-1248), although ethylene oxide or mixtures of ethylene oxide and propylene oxide may also be used.

Suitable silicone fluids are described in U.S. Pat. No. 2,826,551, Geen; U.S. Pat. No. 3,946,500, Jun. 22, 1976, Drakoff; U.S. Pat. No. 4,364,837, Pader; and British Patent 849,433, Woolston. All of these patents are incorporated herein by reference. Also incorporated herein by reference is Silicon Compounds, distributed by Petrarch Systems, Inc., 1984. This reference provides a very good listing of suitable silicone materials.

Another silicone material useful is silicone gum. Silicone gums are described by Petrarch and others including U.S. Pat. No. 4,152,416, May 1, 1979, Spitzer, et al., and Noll, *Chemistry and Technology of Silicones*, New York, academic Press, 1968. Useful silicone gums are also described in General Electric Silicone Rubber Product Data Sheets SE 30, SE 33, SE 54 and SE 76. all of these references are incorporated herein by reference. "Silicone gum" materials denote high molecular weight polydiorganosiloxanes having a mass molecular weight of from about 200,000 to about 1,000,000. Specific examples include polydimethylsiloxane, (polydimethylsiloxane) (methylvinylsiloxane) copolymer, poly(dimethylsiloxane) (diphenyl) (methylvinylsiloxane) copolymer, and mixtures thereof. Mixtures of silicone fluids and silicone gums are also useful herein.

The shampoos herein can contain a variety of other nonessential optional components suitable for rendering such compositions more formulatable, or aesthetically and/or cosmetically acceptable. Such conventional optional ingredients are well-known to those skilled in the art and include, e.g., preservatives, such as benzyl alcohol, methyl paraben, propyl paraben, and imidazolinidyl urea; cationic surfactants, such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; menthol; thickeners and viscosity modifiers, such as block polymers of ethylene oxide and propylene oxide such as Pluronic F88 offered by BaSa Wyandotte, sodium chloride, sodium sulfate, propylene glycol, and ethyl alcohol; pH adjusting agents, such as citric acid, succinic acid, phosphoric acid, sodium hydroxide, sodium carbonate; perfumes; dyes; and sequestering agents, such as disodium ethylenediamine tetraacetate. Such agents generally are used individually at a level of from about 0.01% to about 10%, preferably from about 0.5% to about 5.0%, of the composition.

A typical shampoo composition may comprise (percentages by weight):
 (1) 5–15% active of invention;
 (2) 0–10% anionic coactive;
 (3) 0–10% amphoteric coactive;
 (4) 0–5% lauramide MEA;
 (5) 0–5% thickener;
 (6) 0–2% fragrance;
 (7) 0–1% preservative; and
 (8) remainder water.

In a fourth embodiment of the invention, the surfactant of the invention may be used in a conditioner composition such as is taught and described in U.S. Pat. No. 4,913,828 to Caswell et al. which is hereby incorporated by reference.

More particularly, conditioner compositions are those containing a conditioning agent (e.g. alkylamine compounds) such as those described in U.S. Pat. No. 4,913,828.

A typical condition composition may comprise (percentages by weight):
 (a) 1–98% surfactant of invention, preferably 10 to 60% (or 1–98% or 10 to 60% surfactant mixture comprising the surfactant of invention and wherein cosurfactant(s) are selected from the group consisting of anionics, nonionics, ampholytics, zwitterionics and cationionics);
 (b) 0–80% builder (e.g. , polycarboxylates);
 (c) 0–10% chelating agent (e.g., amino carboxylates);

(d) 0–5% soil release agents (e.g., derivatives of hydroxyether cellulosic polymers);

(e) 0–5% anti redeposition agent (e.g., protease)

(f) 0–2% enzyme (e.g., protease);

(g) 0.01–20% conditioning agent (e.g., cationic surfactant);

(h) 0.1–10% stabilizer for conditioner (e.g., clays or polysaccharide agents);

(i) water and minors to 100%

If formulated as conditioner shampoo, the composition may comprise:

(a) 5–60% surfactant (wholly the surfactant of invention or comprising the surfactant of invention);

(b) 1–60% conditioner (e.g., cationic);

(c) 0–2% preservative (e.g., benzyl alcohol);

(d) 0–10% thickener (e.g., diethanalomide); and (e) remainder water and minors.

In a fifth embodiment of the invention, the surfactant may be used in a cosmetic composition, such as is taught and is described in EP 0,371,803.

Such compositions generally comprise thickening agents, preservatives and further additions.

The composition may comprise polymer thickener in an amount sufficient to adjust the viscosity of the composition, so as to facilitate dispensing it conveniently onto the body surface.

Examples of polymer thickeners include: anionic cellulose materials, such as sodium carboxy methyl cellulose; anionic polymers such as carboxy vinyl polymers, for example, Carbomer 940 and 941; nonionic cellulose materials, such as methyl cellulose and hydroxy propyl methyl cellulose; cationic cellulose materials, such as Polymer JR 400; cationic gum materials, such as Jaguar C13 S; other gum materials such as gum acacia, gum tragacanth, locust bean gum, guar gum and carrageenan; proteins, such as albumin and protein hydrolysates; and clay materials, such as bentonite, hectorite, magnesium aluminum silicate, or sodium magnesium silicate.

Generally, the thickening agent may comprise from 0.05 to 5%, preferably 0.1 to 1% by weight of the composition.

The composition according to the invention can also optionally comprise a preservative to prevent microbial spoilage.

Examples of preservatives include:

(i) Chemical preservatives, such as ethanol, benzoic acid, sodium benzoate, sorbic acid, potassium sorbate, sodium propionate and the methyl, ethyl, propyl and butyl esters of p-hydroxybenzoic acid 2-bromo-2-nitro-propane-1, 3-diol, phenoxyethanol, dibromodicyanobutane, formalin and Tricolsan. The amount of chemical preservative optionally to be incorporated in the composition according to the invention will generally be from 0.05 to 5%, preferably from 0.01 to 2% by weight, the amount chosen being sufficient to arrest microbial proliferation.

(ii) Water activity depressants, such as glycerol, propylene glycol, sorbitol, sugars and salts, for examples alkali metal halides, sulphates and carboxylates. When employing a water activity depressant, sufficient should be incorporated in the composition according to the invention to reduce the water activity from 1 to <0.9, preferably to <0.85 and most preferably 0.8, the lowest of these values being that at which yeasts, molds and fungi will not proliferate.

The composition can also contain other optional adjuncts, which are conventionally employed in compositions for topical application to human skin. These adjuncts, when present, will normally form the balance of the composition.

Examples of optional adjuncts include vehicles, the selection of which will depend on the required product form of the composition. Typically, the vehicle when present, will be chosen from diluents, dispersants or carriers for the dialkyl or dialkenyl phosphate salt so as to ensure an even distribution of it when applied to the skin.

Compositions according to this invention can include water as a vehicle, usually with at least one other cosmetically-acceptable vehicle.

Vehicles other than water that can be used in compositions according to the invention can include liquids or solids as emollients, solvents, humectants, thickeners and powders. Examples of each of these types of vehicles, which can be used singly or as mixtures of one or more vehicles, are as follows:

Emollients, such as stearyl alcohol, glyceryl monolaurate, glyceryl monoricinoleate, glyceryl monostearate, propane-1, 2-diol, butane-1.3 diol, docosan-1,2-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoromethane, monochlorodifluoromethane, trichlorotrifluoromethane, propane, butane, isobutane, dimethyl ether, carbon dioxide, nitrous oxide;

Solvents, such as ethyl alcohol, methylene chloride, isopropanol, acetone, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate.

The cosmetically acceptable vehicle, when present, will usually form from 0.01 to 99.9%, preferably from 59 to 98% by weight of the composition, and can, in the absence of other cosmetic adjuncts, form the balance of the composition.

A wide variety of conventional sunscreening agents, such as those described in U.S. Pat. No. 4,919,934 to Deckner et al. hereby incorporated by reference, may also be used in the cosmetic compositions of the invention.

Such agents include, for example, p-aminobenzoic acid, its salts and its derivatives, anthranilates, salicylates, cinnamic acid derivatives, di- and trihydroxy cinnamic acid derivatives, hydrocarbons such as diphenylbutadiene and stilbene, dibenzalacetone and benzalacetophenone, naphthasulfonates, di-hydroxy naphthloic acid and its salts, hydroxy diphenylsulfonates, coumarin derivatives, diazoles, quinine salts, quinoline derivatives, hydroxy or methoxy substituted benzophenones, uric or vilouric acid, tannic acid and its derivatives, hydroquinone, and benzophenones.

In a sixth embodiment of the invention, the surfactant may be used in a toothpaste composition such as is taught and is described in U.S. Pat. No. 4,935,227 to Duckworth, which is hereby incorporated by reference.

Such compositions generally comprise abrasive gels (e.g. calcium carbonate), oral therapeutic agents (e.g., flourine containing compound), coactives, flavoring agents, sweetening agents, humectants and binding or thickening gels.

Preferred toothpastes of this invention comprise 0 to 1.5% by weight of anionic surfactant. In more preferred products the amount of anionic surfactant is 0 to 1% by weight with most preferred amounts being 0 to 0.75% by weight.

Toothpastes of this invention may include other surfactants, especially non-ionic surfactants.

Toothpaste of the invention will also comprise the usual additional ingredients in particular humectant binder or thickening agent.

Humectants which may be used include glycerol, sorbitol syrup, polyethylene glycol, lactitol, xylitol or hydrogenated corn syrup. The total amount of humectant present will generally range from 10% to 85% by weight of the toothpaste.

Numerous binding or thickening agents have been indicated for use in toothpastes, preferred ones being sodium carboxymethylcellulose, cross-linked polyacrylates and xanthan gum. Others include natural gum binders such as gum tragacanth, gum karaya and gum arabic, Irish moss, alginates, and carrageenans. Silica thickening agents include the silica aerogels and various precipitated silicas. Mixtures of binders and thickeners may be used. The amount of binder and thickening agent included in a toothpaste is generally between 0.1 and 15% by weight.

In a seventh embodiment of the invention, the molecule of the invention may be used in a light duty liquid detergent composition such as those taught in U.S. Pat. No. 4,671,894 to Lamb et al., U.S. Pat. No. 4,368,146 to Aronson et al., and U.S. Pat. No. 4,555,360 to Bissett et al., all of which are hereby incorporated by reference, into the subject application.

Generally such compositions comprise a mixture of sulphate and sulphonate anionic surfactants together with a suds stabilizing agent. These compositions may also comprise nonionic surfactants designed to reduce the level of non-performing ingredients such as solvents and hydrotropes and zwitterionic surfactants for providing enhanced grease and particulate soil removal performance. Among other ingredients which may also be used in such compositions are opacifiers (e.g. ethylene glycol distearate), thickeners (e.g., guar gum), antibacterial agents, antitarnish agents, heavy metal chelators (e.g. ETDA), perfumes and dyes.

A typical light duty liquid composition may comprise (all percentages by weight):

(a) 0.01–65% anionic surfactant;
(b) 0.01–50% surfactant of invention;
(c) 0–8% suds promoting agent (e.g., alkyl alcohol amide);
(d) 0–10% hydrotrope (e.g., benzene sulfonate); and
(e) minors plus water to 100%.

In an eighth embodiment of the invention the molecule of the invention may be used in underarm deodorant/antiperspirant compositions such as those taught in U.S. Pat. No. 4,919,934 to Deckner, U.S. Pat. No. 4,944,937 to McCall and U.S. Pat. No. 4,944,938 to Patini, all of which patents are hereby incorporated by reference.

Such compositions generally comprise a cosmetic stick (gel or wax) composition which in turn generally comprises one or more liquid base materials (e.g., water, fatty acid and fatty alcohol esters, water-insoluble ethers and alcohols, polyorganosiloxanes); a solidifying agent for solidifying the liquid base; and an active component such as bacteriostats or fungistats (for anti-deodorant activity) or astringent metallic salts (for antiperspirant activity).

These compositions may also comprise hardeners, strengtheners, emollients, colorants, perfumes, emulsifiers and fillers.

While various compositions are described above, these should not be understood to be limiting as to what other personal product compositions may be used since other compositions which may be known to those of ordinary skill in the art are also contemplated by this invention.

The invention is set forth in greater detail in the example which follow below. These examples are merely to illustrate the invention and are not intended to be limiting in any way.

EXAMPLE 1

Synthesis of
3-(N,N-dibutylamino)-2-hydroxypropyl-$\beta$-D-galactopyranoside

Acetobromogalactose (2,3,4,6-tetra-O-acetyl-$\alpha$-D-galactopyranosyl bromide) was mixed with allyl alcohol and mercuric cyanide via the Koenigs-Knorr glycosylation to obtain allyl-$\beta$-D-galactopyranoside tetraacetate. This was followed by oxidation with 3-chloroperoxybenzoic acid in dichloromethane to obtain 2,3-epoxypropyl-$\beta$-D-galactopyranoside, 2,3,4,6-0-tetracetate.

In a 35 ml two neck flask was added 0.32 g (0.8 mmoles) of the above identified epoxide compound and 1.5 ml of dry acetonitrile, followed by dropwise addition of N,N-dibutylamine (0.2 g, 1.6 mmoles). The reaction was allowed to run at room temperature and was followed by thin layer chromotography using a 9:1 CHCl$_3$:MeOH with a drop of ammonium hydroxide as eluent. Rf value of the new product was found to be 0.36 (the Rf of starting epoxide prior to consumption had been 0.80).

Column chromatography was used to separate the ring-opened adduct from the excess amine using a 9:1CHCl$_3$:MeOH with a drop of ammonium hydroxide as eluent. Total yield of this syrupy ring-opened product was 0.40 g. The product was confirmed by NMR and M.S.

The product was further deprotected using catalytic amounts of sodium methoxide in 20 ml of anhydrous methanol. TLC (Thin layer chromatography) showed that after 8 hours the product was completely deacetylated. The deacetylated product was passed through a short silica-gel column (8:2 CHCl$_2$:methanol) to yield 0.175 g of the final product, 3-(N,N-dibutylamino)-2-hydroxypropyl-$\beta$-D-galactopyranoside.

EXAMPLE 2

In a 50 ml, 2 neck flask is added 1 gram of 2,3-epoxypropyl $\beta$-D galactopyranoside 2,3,4,6-0-tetraacetate (epoxide compound). 10 ml of anhydrous acetonitrile, and 2-10 equivalents of a primary or secondary amine. Reaction is allowed to stir at 20°-80° C. and is followed by thin layer chromatography using a 9:1 CHCl$_3$:MeOH with a drop of ammonium hydroxide as eluent. More amine can be added to ensure all the epoxide is reacted. The ring-opened product is isolated and the acetate groups are removed if necessary, with catalytic amounts of sodium methoxide in anhydrous methanol. The product is further purified by passing through a silica gel column.

With regard to Examples 1 and 2 above, while it would not necessarily be expected for the 3-(N,N-dibutylamino)-2-hydroxypropyl-$\beta$-D-galactopyranoside of Example 1 to have optimal surfactancy (because of butyl groups), longer chain groups (e.g., C$_6$-C$_{20}$, preferably C$_8$-C$_{14}$) can be prepared in the same manner or as described in Example 2 (where the primary or secondary amine added to epoxide would have, for example, C$_{10}$-C$_{14}$ groups). Preferably, in Example 2, a n-monoalkylamine (e.g., NH$_2$C$_{12}$H$_{25}$) would be used.

EXAMPLE 3

Surface Activity and Detergency

Detergency performance was assessed in triolein removal experiments using Terg-O-Tometer. $^3$H radiolabelled triolein was used to assess soil removal; subsequent to the wash, 4×1 ml samples of wash liquor was removed from each pot and the activity determined using a liquid scintillation counter. Percentage detergency was calculated from the relationship:

$$\% \text{ Detergency} = \frac{A_w}{A_s} \times 100$$

where A$_w$ is the total activity in the wash liquor and A$_s$ is the level of activity originally applied to the cloth.

Wash conditions are given below:

| | |
|---|---|
| Apparatus | Terg-O-Tometer UR 7227 |
| Wash Time | 20 minutes |
| Agitation | 70 rpm |
| Wash liquid volume | 500 mls |
| Dosage | 1 g/l |
| Salt concentration | 0.05M |
| Test cloth | Knitted polyester |
| Soil level | ca. 1.9% |

Figure 2:
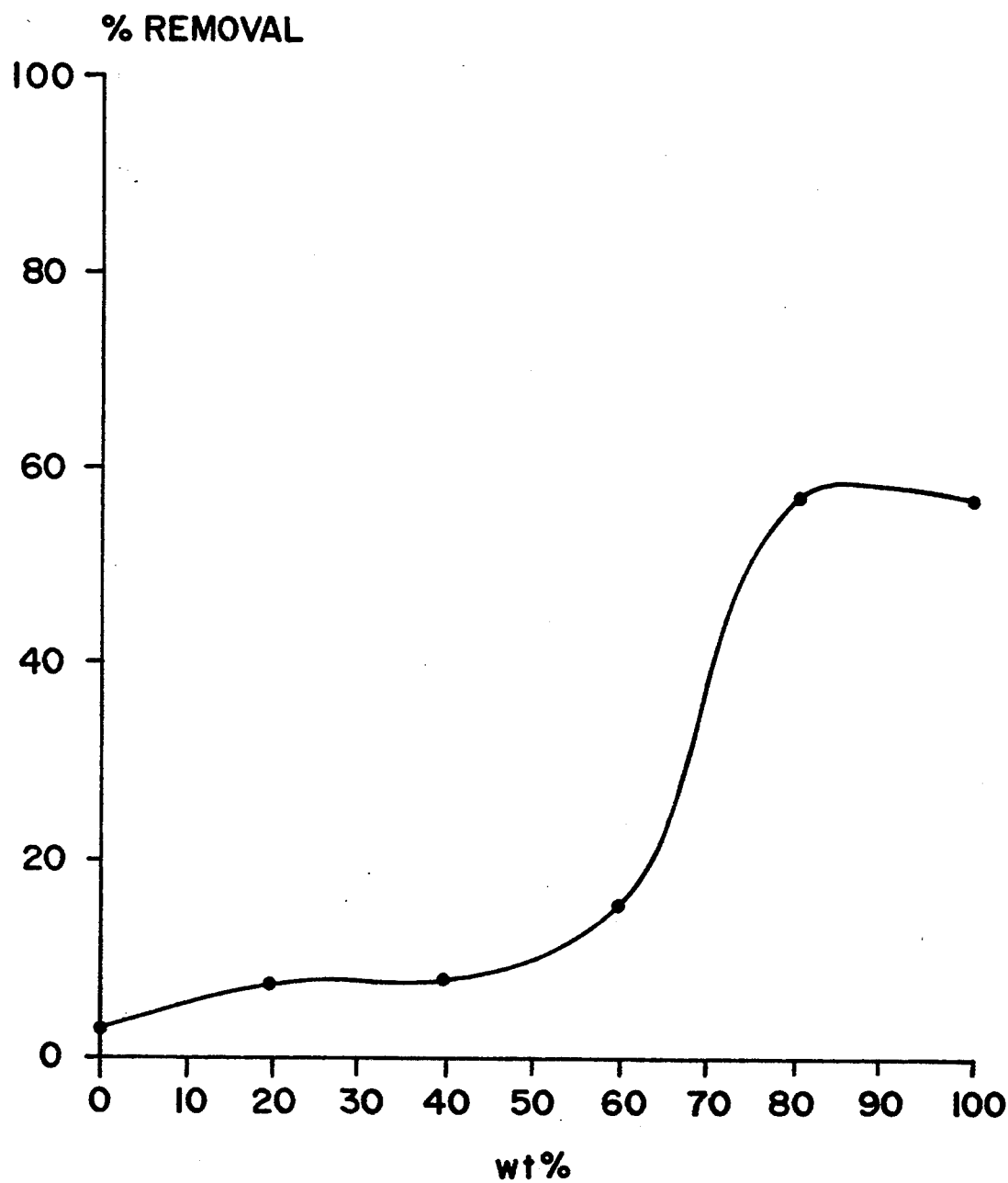
FIG. 2—Graph of the removal of an oily detergent (triolein) from polyester using varying ratios of DHAG and $C_{12}EO_3$ in a borate buffered solution.

The detergency performance of DHAG, in triolein removal experiments at 40° C, with varying ratios of triethylene glycol mono-dodecyl ether (C$_{12}$EO$_3$) is shown in FIGS. 1 and 2 for experiments performed in carbonate and borate buffered solutions respectively, DHAG on its own gives triolein removal of about 58% which is comparable to that obtained with C$_{12}$EO$_8$ or C$_{12}$EO$_6$ alone. Mixtures of DHAG and C$_{12}$EO$_3$ give a small synergistic improvement.

DHAG by itself exhibits good oil soil detergency (about 58% triolein removal at 40° C.). This is comparable to that found for C$_{12}$EO$_6$ or C$_{12}$EO$_8$. When DHAG is mixed with a low HLB surfactant, triethylene glycol mon-dodecyl ether (C$_{12}$EO$_3$), a small degree of synergy is observed. Similar detergency results are obtained whether borate or carbonate-buffered solutions are used.

DHAG appears to be a very promising candidate for the replacement of high HLB ethoxylated surfactants as far as oily soil detergency is concerned.

We claim:

1. A liquid detergent comprising (percentages by weight):
    (a) 5-70% of a detergent active mixture wherein said mixture comprises 65 to 100% of a glyceroglycolipid compound having the structure $$A^1-O-CH_2-\overset{\overset{\displaystyle B}{|}}{CH}-CH_2NRR_1$$

wherein $^1$ comprises one to four saccharide units, R or R$_1$ are the same or different and are hydrogen or a branched or unbranched, saturated or unsaturated, hydrocarbon radical having from about 1 to about 24 carbons; and B is OH or NR$_2$R$_3$, wherein R$_2$ and R$_3$ are the same or different and are hydrogen, a branched or unbranched hydrocarbon, saturated or unsaturated radical having 1 to 24 carbons; wherein the NRR$_1$ group and B group are positionally interchangeable; and
    wherein at least one of R, R$_1$, R$_2$ or R$_3$ must be a hydrocarbon radical having 1 to 24 carbons;
    and wherein said mixture further comprises a nonionic surfactant;
    (b) 0-50% builder;
    (c) 0-40% electrolyte;
    (d) 0.01-5% enzyme;
    (e) 0.1-15% enzyme stabilizer;
    (f) 0-20% phase regulant; and
    (g) remainder water and minors.

2. A liquid detergent according to claim 1, further comprises an additional surfactant which is selected from the group consisting of cationic surfactants zwitterionic surfactants, amphoteric surfactants and mixtures thereof.

* * * * *